(12) United States Patent
Kiedrowski

(10) Patent No.: US 10,561,408 B2
(45) Date of Patent: Feb. 18, 2020

(54) OCULAR DEVICE AND SURGICAL INSTRUMENT HAVING AN OCULAR DEVICE

(71) Applicant: OLYMPUS WINTER & IBE GMBH, Hamburg (DE)

(72) Inventor: Gregor Kiedrowski, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 278 days.

(21) Appl. No.: 15/661,030

(22) Filed: Jul. 27, 2017

(65) Prior Publication Data

US 2017/0319191 A1    Nov. 9, 2017

Related U.S. Application Data

(63) Continuation of application No. PCT/EP2016/050866, filed on Jan. 18, 2016.

(30) Foreign Application Priority Data

Feb. 5, 2015    (DE) .................. 10 2015 202 002

(51) Int. Cl.
*A61B 1/00* (2006.01)
*A61B 17/00* (2006.01)
(Continued)

(52) U.S. Cl.
CPC .... *A61B 17/00234* (2013.01); *A61B 1/00112* (2013.01); *A61B 1/00114* (2013.01);
(Continued)

(58) Field of Classification Search
CPC ............ A61B 1/00112; A61B 1/00124; A61B 1/00126; A61B 1/00128; A61B 1/00195; A61B 1/00197
(Continued)

(56) References Cited

U.S. PATENT DOCUMENTS 4,459,163 A    7/1984  MacDiarmid et al.
4,779,613 A    10/1988  Hashiguchi et al.
(Continued)

FOREIGN PATENT DOCUMENTS

DE        3708124 A1     9/1987
DE      19507205 A1    11/1995
(Continued)

OTHER PUBLICATIONS

International Search Report dated Apr. 6, 2016 issued in PCT/EP2016/050866.
(Continued)

*Primary Examiner* — Matthew J Kasztejna
(74) *Attorney, Agent, or Firm* — Scully, Scott, Murphy & Presser, P.C.

(57) ABSTRACT

An ocular device for a surgical instrument, the surgical instrument having an optical window frame and an optical assembly arranged in an interior space of the surgical instrument, the ocular device including: an ocular window separated from the optical assembly by a space; a holder configured to be connected to the ocular window frame; and at least one elastic element, wherein in a connected state, the at least one elastic element transmits a clamping force from the holder to bias the ocular window towards the space.

9 Claims, 3 Drawing Sheets

(51) Int. Cl.
*A61B 1/04* (2006.01)
*A61B 1/06* (2006.01)

(52) U.S. Cl.
CPC ...... *A61B 1/00124* (2013.01); *A61B 1/00126* (2013.01); *A61B 1/00128* (2013.01); *A61B 1/00195* (2013.01); *A61B 1/00197* (2013.01); *A61B 1/042* (2013.01); *A61B 1/0684* (2013.01)

(58) Field of Classification Search
USPC ................ 600/112, 133, 137; 359/513, 643; 403/348, 322.1
See application file for complete search history.

(56) References Cited

U.S. PATENT DOCUMENTS 5,459,609 A   10/1995   Schrag
5,569,163 A   10/1996   Francis et al.
2013/0267783 A1   10/2013   Davis et al.
2013/0342906 A1   12/2013   Dahmen

FOREIGN PATENT DOCUMENTS

| | | |
|---|---|---|
| DE | 102012011717 A1 | 12/2013 |
| EP | 0501088 A1 | 9/1992 |
| EP | 2674096 A2 | 12/2013 |
| JP | S58-184922 A | 10/1983 |
| JP | S62-188723 U | 12/1987 |
| JP | H06-018788 A | 1/1994 |
| JP | H07-199090 A | 8/1995 |
| JP | H11-221193 A | 8/1999 |
| JP | 2993281 B2 | 12/1999 |

OTHER PUBLICATIONS

Japanese Office Action dated Dec. 11, 2018 in Japanese Patent Application No. 2017-541270.

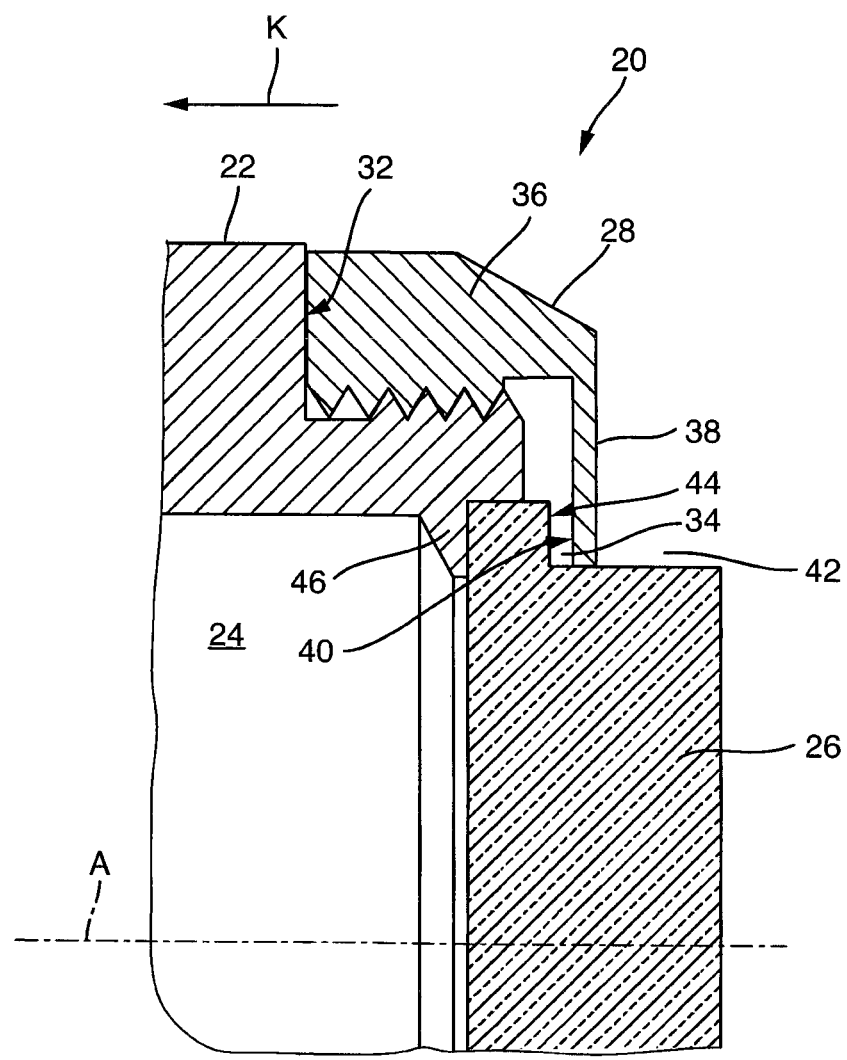

OCULAR DEVICE AND SURGICAL INSTRUMENT HAVING AN OCULAR DEVICE

CROSS-REFERENCE TO RELATED APPLICATION

The present application is a continuation of PCT/EP2016/050866 filed on Jan. 18, 2016, which is based upon and claims the benefit to DE 10 2015 202 002.9 filed on Feb. 5, 2015, the entire contents of each of which are incorporated herein by reference.

BACKGROUND

Field

The present application relates to an ocular device for a surgical instrument, and in particular, to an endoscope, with an optical assembly which can be seated or is seated in an ocular window frame in an interior space of the surgical instrument, wherein the optical assembly is separated from an exterior space by an ocular window, and the ocular window is seated in a holder which is connectible or connected to the ocular window frame, wherein in a connected state, the holder exerts a holding force on the ocular window in a clamping direction. Moreover, the present application relates to a surgical instrument, and in particular, to an endoscope with an ocular device.

Prior Art

Endoscopes for minimally invasive surgery on the human or animal body are generally known. With the assistance of a lens system at the distal tip of the endoscope shaft, it is possible to view a surgical field or investigated field in the body's interior. For this purpose, a plurality of optical assemblies are arranged within the endoscope shaft by means of which light is guided from a body cavity out to a proximal end of the endoscope at which the endoscope is held and operated by a surgeon.

At the proximal end of the endoscope, for example on a handle, there is frequently an eyepiece with an ocular, that is, an optical assembly, from which the light entering the distal tip of the endoscope exits. Such an ocular can be used to directly observe the surgical field with the naked eye. Frequently, a camera head is connected to the ocular so that the surgical field can be observed on a monitor, or the captured image data can be supplied to a connected image processing system. Such an endoscope is known for example from EP 0 501 088 A1.

The optical assemblies in an interior space of the endoscope, for example in its shaft, are separated from each other from an exterior space that surrounds the endoscope by an ocular window.

SUMMARY

It is an object to present an ocular device and a surgical instrument with an ocular device, wherein the hazard of soiling the optical assembly is reduced and hygiene is improved.

Such object can be solved by an ocular device for a surgical instrument, such as an endoscope, with an optical assembly which can be seated or is seated in an ocular window frame in an interior space of the surgical instrument, wherein the optical assembly is separated from an exterior space by an ocular window, and the ocular window is seated in a holder which is connectible or connected to the ocular window frame, wherein in a connected state, the holder exerts a clamping force on the ocular window in a clamping direction, wherein the ocular device comprises at least one elastic element transmitting the clamping force.

In conventional ocular devices of surgical instruments such as ocular devices of endoscopes, frequently a gap remains between the holder and the ocular window frame which serves to compensate for the tolerance when inserting the ocular window. In this region of the surgical instrument, the danger exists, however, of dirt particles collecting which can only be removed with a great deal of effort.

Moreover, the possibility exists of dirt or dust particles penetrating into the interior space of the surgical instrument between the holder and the ocular window and reducing the optical quality of the optical assembly. To clean the optical assembly, it is necessary to remove the ocular window which is associated with significant effort. With the ocular device provided herein, an elastic element is provided which transmits the clamping force. The tolerance compensation which is always necessary accordingly occurs by a more or less strongly preferred elastic deformation of this element. Accordingly, gaps which otherwise may arise from the tolerance compensation are largely avoided.

Moreover, the ocular window is prevented from experiencing great stress while tightening the holder. In this context, the elastic element functions as a damper.

According to one embodiment, the ocular device can be developed in that the elastic element, viewed in the direction of clamping, is at least sectionally arranged between the holder and the ocular window.

This can create a seal between the ocular window and the holder so that dirt or dust particles practically can no longer enter the ocular device.

The elastic element can be a spring element, wherein the spring element can be a disc spring, a spring ring, and/or a wave washer. The elastic element can also be rubber elastic materials, such as in the form of an O-ring.

According to one embodiment, the ocular window frame can comprise a stop for the holder which limits a movement of the holder in the clamping direction.

Such configuration makes it possible to seat the ocular window by the elastic element free of play during installation and then tighten the holder until it contacts the stop. Therefore, a gap between the ocular window frame that surrounds the stop and the holder can be avoided. This improves the hygiene properties of the ocular device, or respectively the surgical instrument, in which the ocular device is installed.

The stop can limit a movement of the holder in the clamping direction so that when the holder is in a fastened state when the holder contacts the stop, a clamping gap exists between the holder and the ocular window viewed in the direction of clamping, wherein the elastic element is arranged at least sectionally in the clamping gap.

Since a clamping gap can be provided structurally between the holder and the ocular window, the ocular window can be prevented from experiencing excessive stress even when the holder is tightened all the way. Therefore, overloading the ocular window, which may be associated with damaging the ocular window, can be avoided.

The holder can comprise an edge that is connectible or connected to the ocular window frame and a collar adjacent thereto, wherein the collar surrounds an opening in which the ocular window is at least partially seated, and wherein the collar comprises a first clamping region on its bottom side facing the ocular window, and wherein the ocular window has a cutout running along its outer perimeter, wherein the ocular window has a second clamping region in the region of the cutout at a top side facing the collar, wherein the elastic element is arranged between the first and second clamping region.

The spring element can comprise a disc spring contacting one side of the holder, such as the bottom side of the collar of the holder, wherein, the disc spring can extend from an outer side of the holder toward a center of the holder starting from a contact region toward its free end.

Therefore, given the provided alignment, or respectively arrangement of the disc spring, the penetration of dirt or dust particles into a region between the ocular window and the holder, and from there continuing toward the optical assembly, can be largely avoided.

The collar can be at least sectionally configured as a spring element. If a part of the holder, such as its collar, is configured as a spring element, a component, i.e., the elastic element itself, can advantageously be discarded. This is in fact formed by the collar of the holder itself. This measure simplifies the production of the ocular device and moreover offers cost advantages.

In addition, the holder can be a union nut, and the union nut can have an inner thread which, in an installed state, meshes with an outer thread on the ocular window frame.

The holder and/or the ocular window frame can be formed of a metal or plastic. The elastic element can also be made of a metal, such as spring steel, or can alternatively be formed of plastic. Also suitable are, for example, rubber or similarly suitable elastic materials. The clamping gap can be between the first and second clamping region. The elastic element can be available, or respectively arranged in the clamping gap. The elastic element can be an O-ring, etc. The ocular window can be designed as an optical flat, i.e., has two plane-parallel surfaces. The ocular window can be circular, as can the ocular window frame. A side edge of the ocular window and the ocular window frame can be constructed to be complementary in terms of form and function. For this purpose, the ocular window can have a cutout in its outer edge in which the holder engages. This side edge of the ocular window can be configured to be ring-shaped. The ocular window frame and the ocular window can be glued to each other. For example, the ocular window can be glued at its outer edge along its perimeter, such as completely along its perimeter, to the ocular window frame. The surgical instrument can be a laparoscope. The aforementioned elements can be applicable to all embodiments.

BRIEF DESCRIPTION OF THE DRAWINGS

Further features will become apparent from the description of embodiments together with the claims and the included drawings. Embodiments can fulfill individual characteristics or a combination of several characteristics.

The embodiments will be described below without restricting the general idea of the invention, based on exemplary embodiments in reference to the drawings, wherein we expressly refer to the drawings with regard to the disclosure of all details that are not explained in greater detail in the text.

FIG. 3 illustrates a schematic and simplified detailed view of the longitudinal section through the ocular device of FIG. 2.

In the drawings, the same or similar types of elements and/or parts are provided with the same reference numbers so that a re-introduction is omitted.

DETAILED DESCRIPTION

Figure 1:
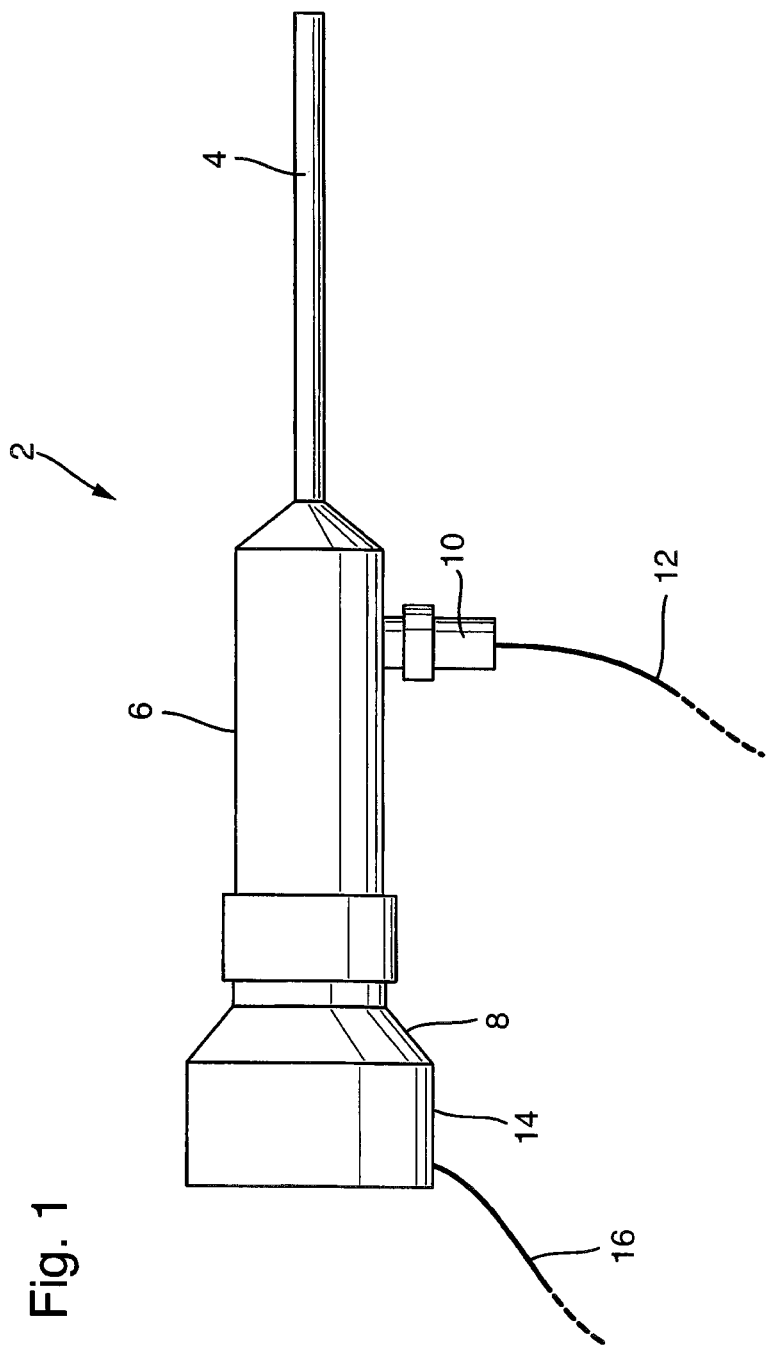
FIG. 1 illustrates a schematic and simplified side view of a surgical instrument.

FIG. 1 shows a schematic and simplified side view of a surgical instrument 2, such as an endoscope. At its distal end, the surgical instrument 2 comprises a tubular shaft 4 with a lens system that makes it possible to observe a surgical or investigated region that lies distally relative to a distal end of the shaft 4. A proximal end of the shaft 4 terminates in a housing 6 that has an eyepiece 8 at a proximal end. The housing 6 is for is handling the surgical instrument 2. On a distal side of the housing 6 is a light source 10 such as an LED light source. The light source 10 is connected by a connecting cable 12 to a suitable power supply.

A schematically portrayed camera head 14 with an ocular adapter (not shown) is arranged on the eyepiece 8. The camera head 14 detects the light exiting the ocular of the surgical instrument 2 with its own lens system, and images it on an optical surface (image) sensor such as a CCD or CMOS chip. The camera head 14 is supplied with power by means of a connection 16. Furthermore, it is possible to send image signals by the connection 16 from the surface sensor of the camera head 14 to an external evaluation unit and transmit control signals to the camera head 14.

Figure 2:
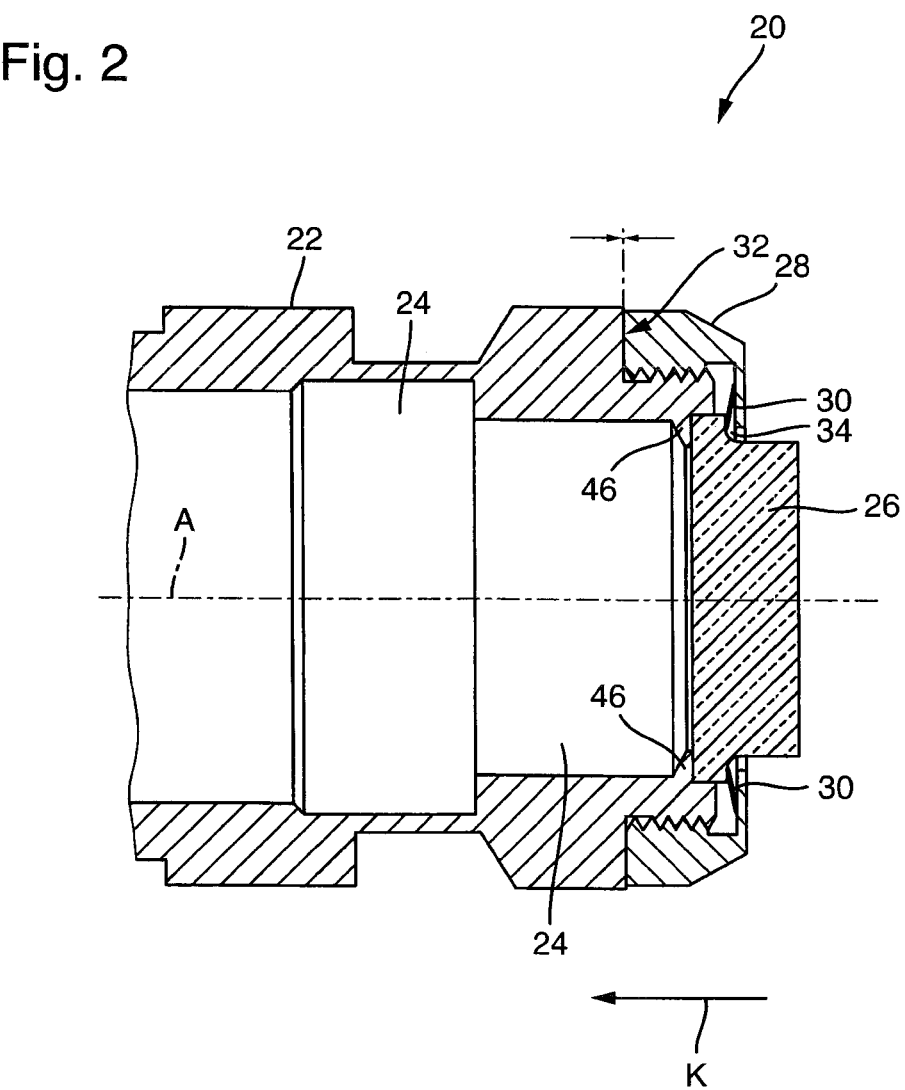
FIG. 2 illustrates a detailed view of an ocular device, in a schematic and simplified longitudinal section.

In a partial schematic simplified longitudinal section, FIG. 2 shows a detailed view of an ocular device 20, such as is provided in the region of the eyepiece 8 at the proximal end of a surgical instrument 2, for example an endoscope.

The ocular device 20 comprises an ocular window frame 22 in which an optical assembly 24 is seated. The optical assembly 24 is for example one or more lenses or lens groups, prisms, filters, etc. that form an optical system. The optical axis A of the optical system is depicted in a dash-dot line. The optical device 20 is located in an interior space of the surgical instrument 2, such as an interior space enclosed by the housing 6 of the endoscope depicted in FIG. 1. The optical system seated thereby serves to image the light beam entering from an investigated region on an image sensor of the camera head 14 at the distal end of the shaft 6.

The camera head 14 is removable. In this state, an ocular window 26 comprising the ocular device separates the exterior space from the interior space of the surgical instrument 2.

The ocular window 26 is seated in a holder 28. A union nut is depicted in FIG. 2 as a holder 28 only as an example. The holder 28 has an inner thread which meshes with an outer thread on the ocular window frame 22. The holder 28 is thereby detachable from or attachable to the ocular window frame 22. In an attached state, which is shown in FIG. 2, the holder 28 exerts a clamping force on the ocular window 26 in the direction of clamping K. That is, the elastic element 30 biases the ocular window 26 towards the window frame 22.

Viewed in the direction of clamping K, at least one elastic element 30 transmitting the clamping force is located between the holder 28 and the ocular window 26. The elastic element is for example a disc spring. However a spring ring, wave washer, elastomer, such as an O-ring, etc. may also be used as the elastic element.

Furthermore, the ocular window frame 22 comprises a stop 32 that limits the movement of the holder 28 in the clamping direction K. The stop 32 limits the movement of the holder 28 in the clamping direction K such that when the holder 28 is in a fastened state as shown in FIG. 2, the holder 28 contacts the stop 32. However, a clamping gap 34 remains between the ocular window 26 and the holder 28. The elastic element 30 is arranged at least sectionally in the clamping gap 34.

In a schematic simplified longitudinal section, FIG. 3 shows a detail of the ocular device 20 of FIG. 2. The holder 28 can be configured such that it surrounds an edge 36 that is connectible to the ocular window frame 22 and a collar 38 adjacent thereto. On its inside facing the ocular window frame 22, the edge 36 is provided with an inner thread. In the direction of the optical axis A, the collar 38 abuts the edge 36 and surrounds an opening through which the ocular window 26 partially extends. In other words, the ocular window 26 is at least partially seated in the opening surrounded by the collar 38.

At its bottom side facing the ocular window 26, the collar 38 has a first clamping region 40. The ocular window 26 has a cutout 42 that runs along its outer parameter. In this region, the ocular window 26 has a second clamping region 44 on its top side facing the collar 38. The elastic element 30 which is not shown in FIG. 3 for reasons of clarity is located between the first clamping region 40 and the second clamping region 44.

The holder 28 is dimensioned such that it contacts the stop 32 of the ocular window frame 22, and a clamping gap 34 remains nonetheless. This prevents excessive pressure from being exerted on the ocular window 26. At the same time, it ensures that a gap in which dirt particles may collect does not arise on the outside between the holder 28 and the ocular window frame 22 where the stop 32 is located.

Furthermore, the penetration of dirt particles or dust into the interior space of the ocular window frame 22 can be avoided. The gap between the holder 28 and ocular window 26 is tightly sealed by the elastic element 30. In this regard, it is particularly advantageous when the elastic element 30, which for example can be a spring element, contacts the bottom side of the collar 38 on one side. The disc spring provided as an elastic element 30 extends starting from a contact region in the direction of its free end from s an outer side of the holder 28 in the direction of its center, i.e., in the direction of the optical axis A. Accordingly as shown in FIG. 2, the contact point between the disc spring and the ocular window 26 lies in the region of a knee point in the cutout 42. This prevents the penetration of dirt or dust particles.

The ocular window frame 22 has a shoulder 46 that extends along the inner space enclosed by the ocular window frame 22, such as completely along the perimeter. On an annular surface of the shoulder 46 facing the ocular window 26, the ocular window 26 is glued to the ocular window frame 22.

According to another exemplary embodiment, the collar 38 of the holder 28 itself is configured at least sectionally as a spring element and hence functions as an elastic element 30.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

REFERENCE NUMBER LIST

2 Surgical instrument
4 Shaft
6 Housing
8 Eyepiece
10 Light source
12 Connecting cable
14 camera head
16 Connection
20 Ocular device
22 Ocular window frame
24 Optical assembly
26 Ocular window
28 Holder
30 Elastic element
32 Stop
34 Clamping gap
36 Edge
38 Collar
40 First clamping region
42 Cutout
44 Second clamping region
46 Shoulder
A Optical axis
K Clamping direction

What is claimed is:

1. An ocular device for a surgical instrument, the surgical instrument having an optical window frame and an optical assembly arranged in an interior space of the surgical instrument, the ocular device comprising:
   an ocular window separated from the optical assembly by a space;
   a holder configured to be connected to the ocular window frame; and
   at least one elastic element, wherein in a connected state, the at least one elastic element transmits a clamping force from the holder to bias the ocular window towards the space;
   wherein the holder comprises an edge connected to the ocular window frame and a collar adjacent to the edge, wherein the collar surrounds an opening in which the ocular window is at least partially seated, and wherein the collar comprises a first clamping region on its bottom side facing the ocular window, and wherein the ocular window has a cutout running along its outer perimeter, wherein the ocular window has a second clamping region in the region of the cutout at a side facing the collar, wherein the elastic element projects between the first and second clamping regions; and
   the elastic element comprises a disc spring contacting one side of the holder.

2. The ocular device according to claim 1, wherein the elastic element when viewed in a direction of biasing, is at least sectionally arranged between the holder and the ocular window.

3. The ocular device according to claim 1, wherein the ocular window frame comprises a stop for the holder which limits a movement of the holder in a biasing direction.

4. The ocular device according to claim 3, wherein the stop limits a movement of the holder in the biasing direction such that when the holder is in a connected state when the holder contacts the stop, a clamping gap exists between the holder and the ocular window when viewed in the biasing direction, wherein the elastic element is arranged at least sectionally in the clamping gap.

5. The ocular device according to claim 1, wherein the disc spring extends from an outer side of the holder toward a center of the holder starting from a contact region toward a free end.

6. The ocular device according to claim 1, wherein the collar is formed at least sectionally as an elastic element.

7. The ocular device according to claim 1, wherein the holder is a union nut having an inner thread which, in a connected state, meshes with an outer thread on the ocular window frame.

8. A surgical instrument comprising the ocular device according to claim 1.

9. The surgical instrument of claim 8, wherein the surgical instrument is an endoscope.

* * * * *